United States Patent [19]

Bergström et al.

[11] Patent Number: 5,766,460

[45] Date of Patent: Jun. 16, 1998

[54] LIQUID CHROMATOGRAPHIC SYSTEM

[75] Inventors: Jan Bergström, Bälinge; Lennart Söderberg, Upsala, both of Sweden

[73] Assignee: Pharmacia Biotech AB, Upsala, Sweden

[21] Appl. No.: 779,059

[22] Filed: Jan. 6, 1997

Related U.S. Application Data

[63] Continuation of Ser. No. 428,186, filed as PCT/SE93/00913 Nov. 2, 1993 published as WO94/09879 May 11, 1994, abandoned.

[30] Foreign Application Priority Data

Nov. 2, 1992 [SE] Sweden ................ 9203222

[51] Int. Cl.$^6$ ................................................ B01D 15/08
[52] U.S. Cl. ........................................ 210/198.2; 210/656
[58] Field of Search ........................ 210/198.2, 232, 210/238, 656, 659

[56] References Cited

U.S. PATENT DOCUMENTS

| | | | |
|---|---|---|---|
| 3,575,295 | 4/1971 | Yoshida | 210/198.2 |
| 3,583,230 | 6/1971 | Patterson | 210/198.2 |
| 3,630,371 | 12/1971 | Hadina | 210/198.2 |
| 4,089,207 | 5/1978 | Patton | 73/23.1 |
| 4,154,583 | 5/1979 | Favre | 210/198.2 |
| 4,155,846 | 5/1979 | Novak | 210/198.2 |
| 4,175,037 | 11/1979 | Benney | 210/198.2 |
| 4,364,263 | 12/1982 | Sankoorikal | 210/198.2 |
| 4,394,263 | 7/1983 | Dosch | 210/198.2 |
| 4,446,105 | 5/1984 | Dismore | 210/198.2 |
| 4,451,365 | 5/1984 | Sattler | 210/198.2 |
| 4,551,251 | 11/1985 | Kolobow | 210/198.2 |
| 4,719,011 | 1/1988 | Shalon et al. | 210/198.2 |
| 4,724,081 | 2/1988 | Kawahara | 210/198.2 |
| 4,840,730 | 6/1989 | Saxena | 210/198.2 |
| 4,857,187 | 8/1989 | Ito | 210/198.2 |
| 4,877,523 | 10/1989 | Nunogaki | 210/198.2 |
| 4,900,435 | 2/1990 | Anderson | 210/198.2 |
| 4,966,695 | 10/1990 | Joshua | 210/198.2 |
| 5,004,547 | 4/1991 | Grunfeld | 210/198.2 |
| 5,071,547 | 12/1991 | Cazer | 210/198.2 |
| 5,117,109 | 5/1992 | Asakawa | 210/198.2 |
| 5,417,853 | 5/1995 | Mizuno | 210/198.2 |

FOREIGN PATENT DOCUMENTS

| | | | |
|---|---|---|---|
| 0078435 A2 | 10/1982 | European Pat. Off. | 210/198.2 |
| WO 90/06507 | 6/1990 | WIPO | 210/198.2 |
| WO 92/04958 | 4/1992 | WIPO | 210/198.2 |

OTHER PUBLICATIONS

Derwent Abstract No. 87–011839/02 of Japan Patent No. 61270658 Nov. 29, 1986.

*Primary Examiner*—Ernest G. Therkorn
*Attorney, Agent, or Firm*—Dinsmore & Shohl LLP

[57] ABSTRACT

A liquid chromatographic system comprises at least two modules, at least one fluid flow line, and at least two connector devices provided along the flow line and respectively connecting the modules to the flow line. One of the two modules comprises a separation module and the other of the two modules comprises an ancillary module having a non-separation function. Each of the two modules includes at least one end connector fit into the respective connector device, and each end connector is adapted to interchangeably fit into either connector device.

20 Claims, 11 Drawing Sheets

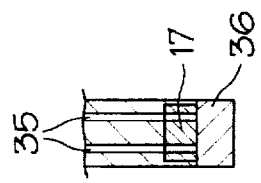
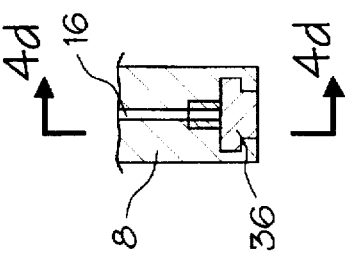
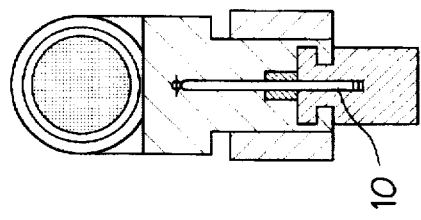
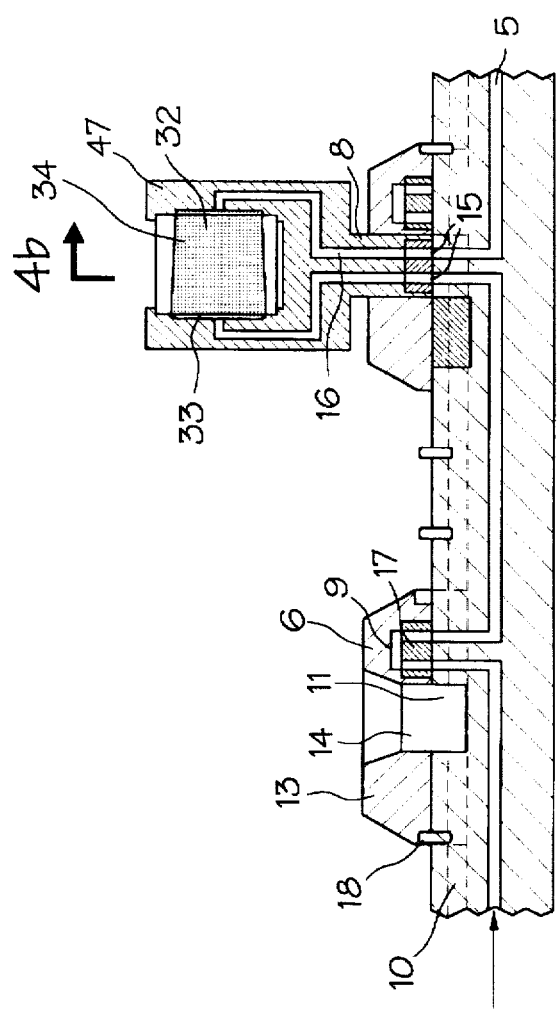

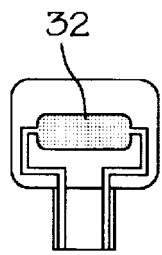
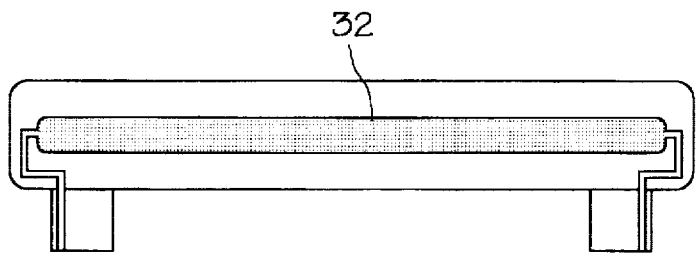
FIG. 5A  FIG. 5B
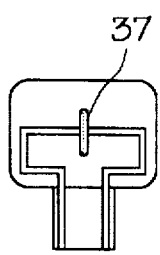
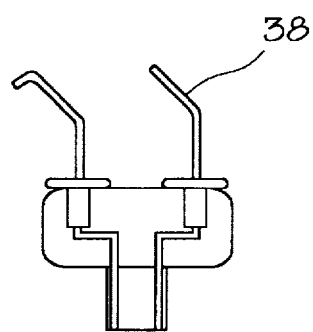
FIG. 6  FIG. 7
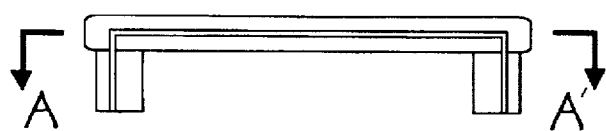
FIG. 8a
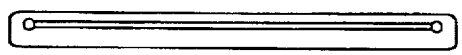
FIG. 8b
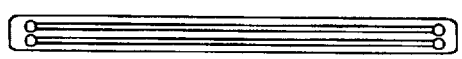
FIG. 8c
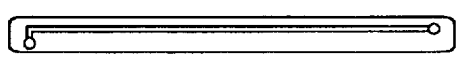
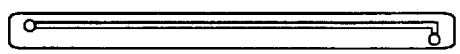
FIG. 8d
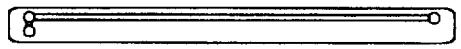
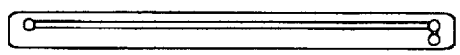
FIG. 8e

LIQUID CHROMATOGRAPHIC SYSTEM

This is a continuation of application Ser. No. 08/428,186, filed as PCT/SE93/00913, Nov. 2, 1993 published as WO94/09879 May 11, 1994 now abandoned.

TECHNICAL FIELD AND BACKGROUND OF THE INVENTION

The present invention relates to a liquid chromatographic system which includes one or more flow lines that pass through a plurality of units (modules) having functions that can be used in chromatography. The flow lines and units may be fixedly mounted on an appropriate stand (frame), for instance a base plate.

The functional units of earlier described systems include chromatographic columns, filters, valves, branches, and connections which operate to lead liquid from and to the system, injection ports, for instance for charging samples, detector connectors, and so on. In the earlier described systems, these units are mutually connected together with the aid of flexible tubings. A common feature of the known systems is that they shall enable eluants, such as buffers and solvents, for instance, to be mixed and introduced in a predetermined order and at predetermined positions.

The connection between a module and a flow line is made through an end-connecting means on the module and a connecting device on the flow line.

The systems often use small particles as the separation medium, which requires the application of high pressures, particularly when high resolution is desired. The apparatus arrangements and the various tubing connections have resulted in highly complicated "plumbing" tubing-based systems which are not easy to follow. Such systems are normally encumbered with such problems as leakage, the ingress of air and wrongly connected tubings, both when the system is connected-up and when wishing to exchange or replace a unit in the system. In order to operate these systems, it is often necessary to be an expert in chromatography and also a good instrument technician.

A module/system for chromatographic columns has previously been disclosed in U.S. Pat No. 4,719,011. An exchangeable column with end-connecting means and connecting devices has been described in WO-A-9204958.

OBJECTS OF THE INVENTION

The object of the present invention is to provide a system which is of simple construction, which can be viewed without difficulty and which includes readily exchangeable units and, in principle, will include no tubing bundles or hanks. The invention presents a new user interface in liquid chromatography and has the function of the system placed in focus. When developing the invention, particular thought has been given to the possibility of testing strategies quickly and simply in conjunction with the development of complex chromatographic methods within the framework of research and industrial separation processes, including laboratory, pilot plant and final industrial processes. Another object of the invention is as a teaching aid in schools and educational institutions.

BRIEF DESCRIPTION OF THE DRAWINGS

Different exemplifying embodiments of the invention are illustrated in FIGS. 1–17. The variant most preferred at present is illustrated in detail in FIGS. 1–13. Components which have analog functions are identified with the same reference signs in the various Figures.

FIG. 1 is a front view (with the plate placed vertically) and illustrates the basic structure.

FIG. 4 illustrates in FIG. 4a the base plate of FIG. 1 when seen from one side in a longitudinal plane through a flow line to which a separation module (4) is connected. FIG. 4b is a sectional view taken on the line A—A' of FIG. 4a. FIG. 4c contains two mutually perpendicular section views of the lower part (the end-connector) of a disconnected module.

FIGS. 5a and 5b illustrate separation modules having one and two end-connecting means respectively.

FIG. 6 illustrates a filter module.

FIG. 7 illustrates a module for connection to an outer unit.

FIG. 8a is a side view of a flow bridge intended to conduct flow between two connecting devices.

FIGS. 8b–8e illustrate top views of variants of flow bridges, respectively.

SUMMARY OF THE INVENTION

Figure 1:
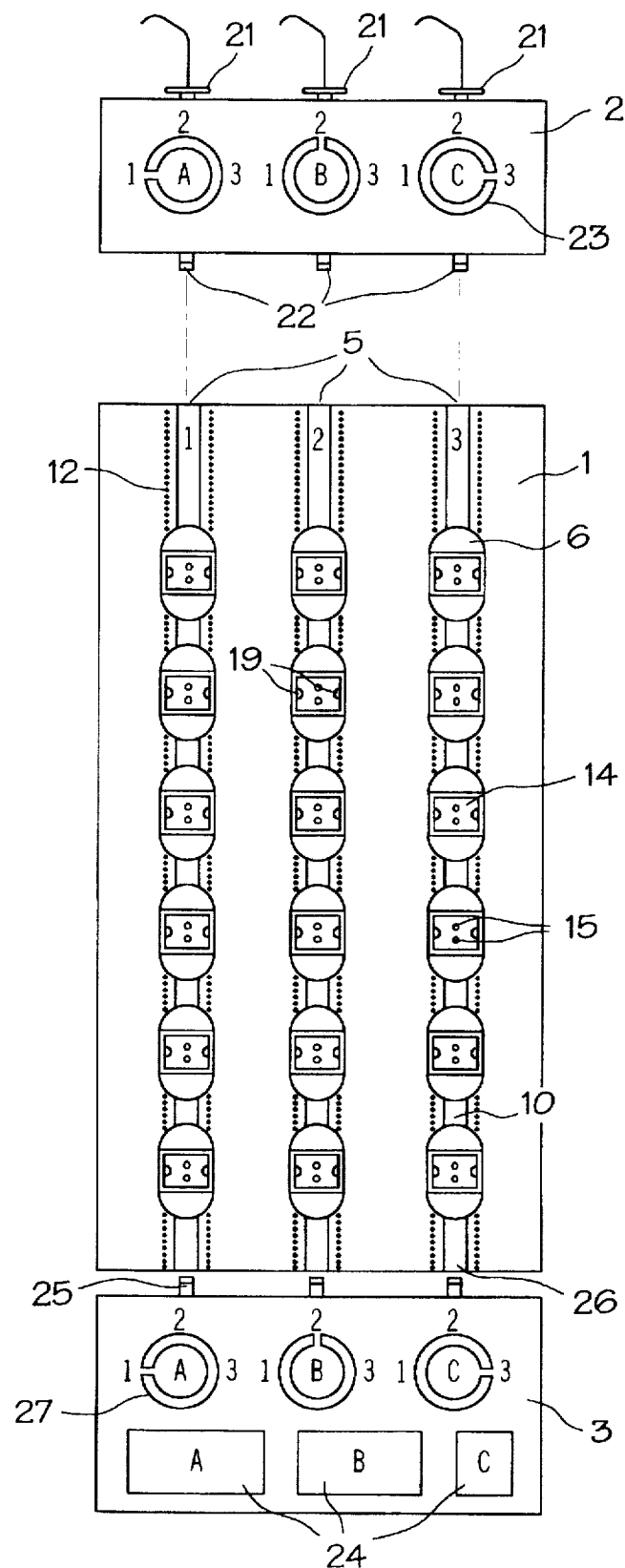
FIG. 1 illustrates an embodiment which includes a base plate (1) as a base unit, and two different end-pieces (2,3), which form ancillaries.

The invention is characterized in that the modules have end-connecting means which enable them to be connected in any desired sequence to connecting devices in the flow lines of the system. The couplings provided by the end-connecting means will preferably be quick-couplings, by which is meant that the flow channel of a module can be sealingly connected to the flow line in a connecting device by a simple joining movement, optionally with a pressing, rotating or sliding manipulation. A quick-coupling will normally have a holding function. Examples of quick-couplings include bayonet couplings, snap-in couplings, slide couplings, etc. Couplings of the kind which are screwed together are not included in the term quick-coupling.

One variant of the invention resides in a chromatography system of the kind defined in the introduction and is characterized in that it includes (a) at least one flow line (5) which includes along its length two or more devices (6) (connecting devices) by means of which a module (7) having the function described below can be connected operationally; and (b) at least one separation module and optionally at least one further module, wherein said module or further module has one or more end-connecting means (8) which are geometrically and functionally adapted to said connecting device (6) so that modules (7) that are provided with such end-connecting means (8) can be functionally connected to any of said connecting devices (6).

DETAILED DESCRIPTION

General

The variants illustrated in FIGS. 1, 4 and 15–17 include a base plate/stand (1) and normally from 1 to 10, preferably 2 to 4, flow lines (5). The variant illustrated in FIG. 14 has no base plate/stand.

Two or more connecting devices (6) are fitted along each flow line, for connecting modules thereto. For each connecting device, for instance integrated therein, there may be located a part (9) of a flow line which enables the module to be bypassed when its function is deactivated. According to the invention, the most practical embodiments will include at least two and at most 15–25 connecting devices (6) along one and the same flow line (5). The connecting devices are normally spaced apart at regular intervals along a given flow line (5). Each flow line (5) on one and the same base plate (1) will normally have the same number of connecting devices (6). In order to increase the utility of the system, the flow lines will normally extend parallel to each other with the same distance between two adjacently located flow lines.

The Base Plate

The base plate (1) of the embodiments illustrated in FIGS. 1 and 4 includes guide means (10) to which the connecting devices (6) are movably fitted. The guide means (10) may have the form of rails or milled grooves which extend along the flow lines (5) between end-positioned connecting devices. The guide means may have a T-shaped cross-section. Alternatively, the guide means may extend perpendicularly to the flow lines and/or each connecting device may have its own guide means. The guide means are normally attached directly to the base plate (1) in the vicinity of their respective flow lines (5). In the case of the embodiments illustrated in FIGS. 1 and 4, flow lines are built into the guide means (10). The guide means and the base plate may be formed integrally with one another from a single material blank.

As illustrated in FIG. 4a, the base plate (1) or a part firmly joined thereto may be provided in the vicinity of the connecting device (6) with a recess (11) which is able to accommodate the bottom part of the end-connecting means (8) of connected modules. The embodiment illustrated in FIG. 4a has recesses (11) that are located on the guide means (10).

One or more lines/conductors (12) for signal and power transmission from or to connected modules may be arranged in the base plate (1), preferably along the flow lines (5). Transmission may be effected through the medium of optical or electrical signals, or through the medium of pressure changes, etc. The signals may correspond to the values measured in connected detector cells, these signals being transmitted through the lines/conductors (12) to a suitable signal processing unit, where the signals are converted into physical magnitudes. Measured signals may also be used to control a connected module, via the signal processing unit and the lines/conductors (12). The signal processing unit(s) may be a computer which is either incorporated in the system (for instance along lines (12), in modules (see FIG. 10), or in connecting devices) or connected externally (not shown in the drawings).

General purpose function units for measuring flow, conductivity, detecting purposes etc may be built in along the flow lines at one or more positions, for instance in the connecting devices or vicinity thereof.

In the case of the embodiment at present preferred, at least three of the connecting devices (6) lie in one and the same plane.

The base plate (1) may be constructed so that several plates can be connected in series or in parallel. Compare FIG. 3.

The Connecting Device

The main parts of the connecting device (6) are comprised of a holder (13) for a module (7), and a valve function for bypassing and/or connecting flow when a module has been placed in the holder (13). In a simple form, the valve function may consist of a tap (not shown in the drawings). A valve function will be described with reference to FIG. 4a. The valve function of the FIG. 4 embodiment is coupled to a module connecting mechanism. The valve function may also be a separate function which is free from the connecting mechanism.

In the embodiment illustrated in FIGS. 4a–b, the connecting device (6) includes a holder (13) for a module (4, 7). The holder (13) has a through-penetrating aperture (14) which faces towards the recess (11). The connecting device (6) is movable along its associated guide means (10). When the connecting device is moved along the guide means (10), the flow-line part (9) is disconnected thereby exposing openings (15) in the flow line (5) that in turn become connected to the flow channels (16) of a module placed in the aperture (14). openings in flow lines and/or their associated channels may be fitted with elastic sealing elements (17), to reduce the risk of leakage.

The guide means (10) may be provided with a so-called positioning device in the form of pins (18), for instance, in order to define a fixed movement for deactivation and/or activation of the connecting device. As illustrated in FIG. 4a, the connecting device may have corresponding recesses.

The enlarged part of FIG. 1 shows a top view of a connecting device. The connecting device has been displaced along its guide means (10), so that the openings (15) in the flow line (5) will be seen in the aperture (14) of said device. The means includes contacts (19) for connecting the line/conductor (12) to contacts (20) on a connected module (see FIG. 10).

The End-Pieces

End-pieces (2 and 3), which have mutually different functions can be connected to the flow line on the base plate. The FIG. 1 embodiment includes a detachable end-piece (2) which is intended to conduct and distribute flow to the flow lines in an inventive base plate. The end-piece has inlets (21) for supplied liquids (including solutions, buffers, mixtures) and liquid outlets (22). The outlets match the inlets in the base plate. The number of inlets (21) and outlets (22) may be the same or different and may differ from the number of flow lines (5) in the base plate (1). The end-piece (2) includes a control means (23) for mixing and/or guiding incoming flows to predetermined outlets (22) in a predetermined and controllable manner. This control may be manual or automated with programmable control means.

The FIG. 1 illustration also includes a detachable end-piece which is intended for connection to the outlet end of a base plate and which enables different sample handling functions (24) to be connected. The end-piece (3) has a number of inlets (25) for connection to the outlets (26) of respective flow lines in the base plate (1). Classic functions can be connected and may possibly also be integrated in the end-piece (3) to a greater or lesser extent. Examples in this regard are functions for waste, collecting fractions and transferring eluate to different external units. The end-piece (3) may be provided with control means (27) for enabling a correct flow line (5) to be guided to a desired sample handling function. This control of the end-piece (3) may be analogous with the control of the end-piece (2).

Figure 2:
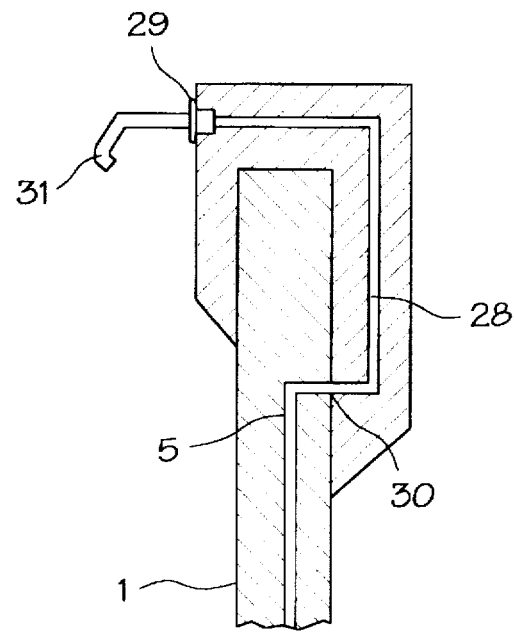
FIG. 2 illustrates an alternative method of connecting the flow by means of an end-piece.

FIG. 2 illustrates a method of connecting the end-pieces. The end-piece of this embodiment includes a flow channel (28) having an inlet (29) and an outlet (30) enabling the connection of one or more external tubing (31). The end-piece is configured so as to enable it to be fitted over one end of the base plate (1), so that its outlet (30) is connected functionally to one of the flow channels (5) of the base plate, with the aid of the quide means (10). The end-piece may contain the same functions as the end-piece of the FIG. 1 embodiment. The end-piece shown in FIG. 2 intended for base plates according to FIG. 1 may be provided with milled grooves or with rails which match the guide means (10).

Figure 3:
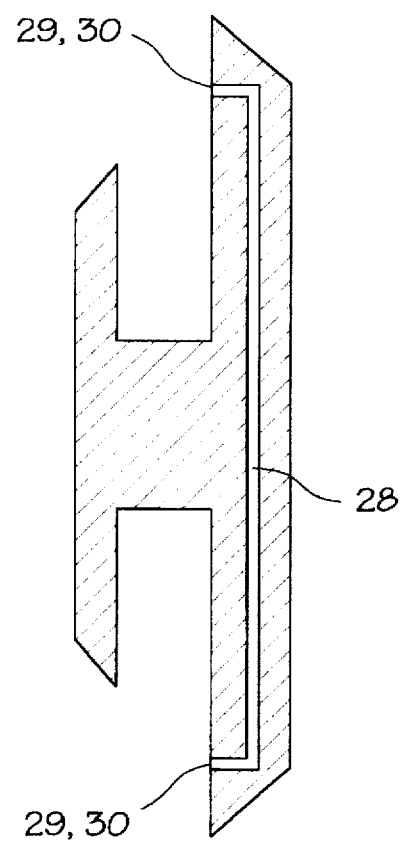
FIG. 3 illustrates a connector for connecting together two base plates.

FIG. 3 illustrates a connecting piece for connecting together two base plates. The principle of connecting to a base plate is the same as that illustrated in FIG. 2.

Modules Described with a Starting Point from a Separation Module

FIGS. 4a–c illustrate an embodiment of a separation module (4) which contains a separation medium (32), flow channels (16), a flow spreading/collecting function (33 and 34 respectively) and an end-connecting means (8). When the module is not used, the openings (35) in the module flow channels are normally covered by closure means (36) to avoid air bubbles and dehydration. In the illustrated embodiment, the closure device (36) is T-shaped and fits into a T-shaped groove milled in the end-connecting means. When the closure device is displaced sideways, openings (35) in the flow channels are exposed. The openings (35) will preferably be surrounded by a sealing element (17) which presses against the closure device (36).

The outer shape of the end-connecting means (8) are the same for modules having different functions when they are to be used on the same base plate. By "the same" is meant that they fit a plurality of holders (13) in one and the same inventive system. In a connected state, the configuration of the flow channel openings (35) matches the openings (15) in the flow line (5), so as to enable flow to pass through.

FIGS. 4a–c illustrate a variant of possible module connection functions. When the module is placed in the aperture (14), the closure device (36) and the T-shaped milled groove of the end-connecting means (8) are located on the bottom of the recess (11), the recess is formed so that no space in form of play will be found between the closure device and the bottom of the recess. When a module (4) is inserted in the connecting device (6) and said device is moved along the guide means (10), the milled T-groove of the end-connecting means matches the T-shape of the T-shaped rail of the guide means, which means that the closure device (36) remains in the recess (11) and the openings (35) of the flow channels are exposed. Upon completion of this movement, the openings (35) match corresponding openings (15) in the flow line (5). The T-shape of the guide means (10) and the milled groove in the end-connecting means fix the module in the holder (14). When movement is completed, liquid is able to flow into the module and, when appropriate, may be returned to one of the existing flow lines (5). The sealing element (17) presses resiliently against the upper surface of the guide means, to provide a sealing effect.

When the connecting device (6) is moved back to its original position, so as to disconnect the module (4), the closure device (36) is caught by the T-groove milled in the end-connecting means, thereby closing the module. The flow of liquid is caused to bypass the module, through the flow-line part (9).

Types of Modules

FIGS. 5–12 illustrate different types of modules. A common feature of the illustrated modules is that they have one or more, preferably 1–2 end-connecting means with associated flow channels and a functional part through which liquid shall flow, be mixed, branched-off or stopped. The flow channels are emphasized in the Figures by heavy black lines. The end-connecting means of respective modules are shown schematically. The requirements for a geometric shape that is adapted to the connecting device and flow channels are the same as those mentioned above with respect to a separation module. The modules may be provided with closure device analogous with that described with reference to FIG. 4.

FIGS. 5a and 5b illustrate separation modules which include a separation medium in the form of a matrix (32) and flow channels. The module illustrated in FIG. 5a has an inlet and an outlet through a common end-connecting means, and the module illustrated in FIG. 5b through separate ends. The end pieces of the separation medium have spreading and collecting functions respectively, which can be achieved with the aid of filter paper inserts, end-piece abutment surfaces with inlets combined with systems of channels, etc. (33 and 34 in FIG. 4a). The matrix (32) may be comprised of discrete, packed particles of cross-linked polysaccharide, polyacrylamide, and the like, or may be continuous (monolithic), i.e. have the form of a porous body. The matrix may exhibit substituents enabling the desired type of chromatography to be run (e.g. ion exchange groups, hydrophobic groups, affinity ligands). The width and the length of the matrix are determined by the separation performance desired. The matrix may be given the form of a membrane. It is believed that the future preferred embodiments of the invention will comprise matrixes in form of a continuous body with a cylindrical or frusto conical shape, narrowing in the flow direction of the column (see FIGS. 4a–b).

FIG. 6 illustrates a filter module which includes flow channels having an inlet and an outlet, a common end-connecting means and a filter (37). The filter may consist of material conventional for chromatography. Although not shown, filter modules may also have two end-connecting means.

FIG. 7 illustrates a connecting module. The module has an end-connecting means and two separate flow channels, each provided with an inlet and an outlet. External units for sample handling, detection, etc., can be connected to the module by means of tubings (38). Flow from a connected external unit can be passed back to the module and from there to the flow line of the base plate through one of the tubings. This type of module may be provided with two or more end-connecting means (not shown).

FIG. 8a illustrates a flow bridge which is intended to conduct liquid flow from one connecting device to another. Flow bridges may also have three or more end-connecting means in order to bridge to more than two flow lines/connecting devices.

FIGS. 8b–e illustrate different variants of the bridge shown in FIG. 8a and show how the bridge can be configured to conduct and distribute flow between the flow lines in the base plate. The bridges are shown in a sectional view taken on the line A—A' in FIG. 8a. The solid rings symbolize an inlet or outlet coming from beneath. The bridges illustrated in FIG. 8e include the possibility of mixing or dividing flow.

Figure 9:
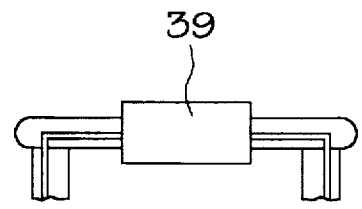
FIG. 9 illustrates a flow bridge with a symbol for an incorporated function (the rectangle).

FIG. 9 illustrates a bridge where the rectangle (39) symbolizes that a flow bridge may incorporate an optional function in the form of valves, filter, matrices, additional connection, detectors, etc.

Figure 10:
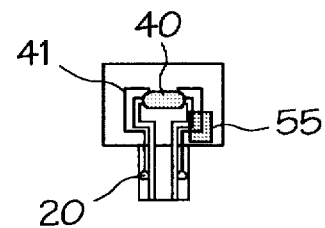
FIG. 10 illustrates an example of a detector cell.

FIG. 10 illustrates a detector module. The detector unit (40) may be based on pH, UV, IR, conductivity, capacitance, refractive index, etc. The transmission of signals from the module is effected through lines/conductors (41) and contacts (20) to corresponding contacts (19—shown in FIG. 1) in the connecting device. Correspondingly, other modules (for instance valve modules) may be provided with power and signal transmission lines/conductors. Detector modules may be equipped with signal processing units (55).

Figure 11A:
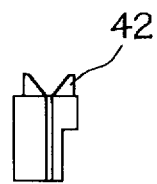
FIGS. 11a–11c illustrate different forms of sample injection devices (ports and loops).
Figure 11B:
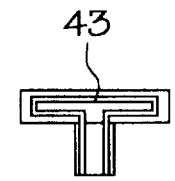
Figure 11C:
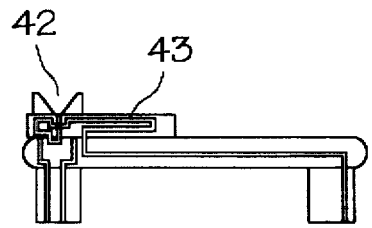

FIGS. 11a–c illustrate modules that can be used in conjunction with sample application. FIG. 11a illustrates a simple sample injection module which includes a through-passing flow channel with an injection port (42) at one end thereof. FIG. 11b illustrates a sample loop module which includes a loop (43), an end-connecting means and a flow channel. Modules according to FIGS. 11a and 11b are preferably used together. These modules can be connected consecutively, one after the other, along one and the same flow line, whereafter the loop (43) can be filled by injecting sample through the port (42). Subsequent to being filled, the loop (43) can be moved to an appropriate position in the system set-up. FIG. 11c illustrates a bridge module having an injection port (42) and a loop which can be moved laterally (as shown by the double-headed arrow). FIG. 11c shows the loop (43) in a sample-charging position. The loop is filled as sample is injected. Surplus sample is passed to the right end-connecting means. As the loop is moved sideways to the left (the injection position), it is connected to the left end-connecting means and the sample can be passed into the flow line connected to this end. Displacement of the loop creates a valve function which may, in principle, be constructed in a similar fashion to the valve function in FIG. 4.

Figure 12A:
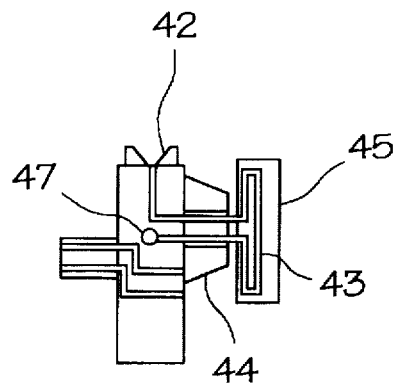
FIGS. 12a and 12b illustrate a variant of an injection port which is connected to a loop and to a container for surplus sample (wastes).
Figure 12B:
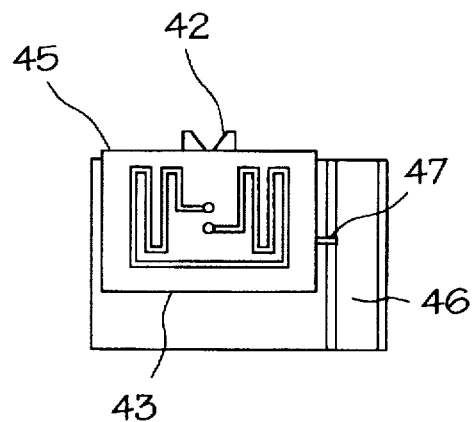

FIGS. 12a and 12b illustrate a module having a connecting device (44) for a sample loop module (45). The module also includes an injection port (42), a vessel for waste (46), flow channels and an end-connecting means. The module illustrated in FIG. 12b is a front view of the module illustrated in FIG. 12a. The connecting device (44) may be constructed analogously with what has been described with reference to FIGS. 4a–b. The sample loop module may be the same as that shown in FIG. 11b. FIGS. 12a–b show the loop in its charging position. The loop (43) is filled by injecting sample through the port (42), and excess sample is passed to the waste vessel (46) through the channel (47). When the connecting means (44) with a connected loop is displaced downwards, the loop is connected functionally to the flow channels in the end-connecting means of the module (the injection position). The connection to the waste vessel is disconnected at the same time. In the injection position, the loop contents can be passed to the flow line to which the end-connecting means is coupled.

FIGS. 12a–b show that a module may have both an end-connecting means and a connecting device. The principle can be applied to modules having other functions and enables the inventive system to be extended in several dimensions without the aid of bunches of tubings. Compare FIGS. 14–17, particularly FIG. 14.

A so-called stop module, i.e. a module which completely lacks a flow channel through the end-connecting means is one example of such additional modules.

One and the same module may include two or more of the functions mentioned in connection with FIGS. 5–12. Thus modules carry at least one function selected from the group consisting of separation, filtration, connector for one or more external unit(s), valve, conductor for liquid flow between two or more flow lines/connecting devices, injection port for liquids, loop of samples, detector and stop.

Figure 13:
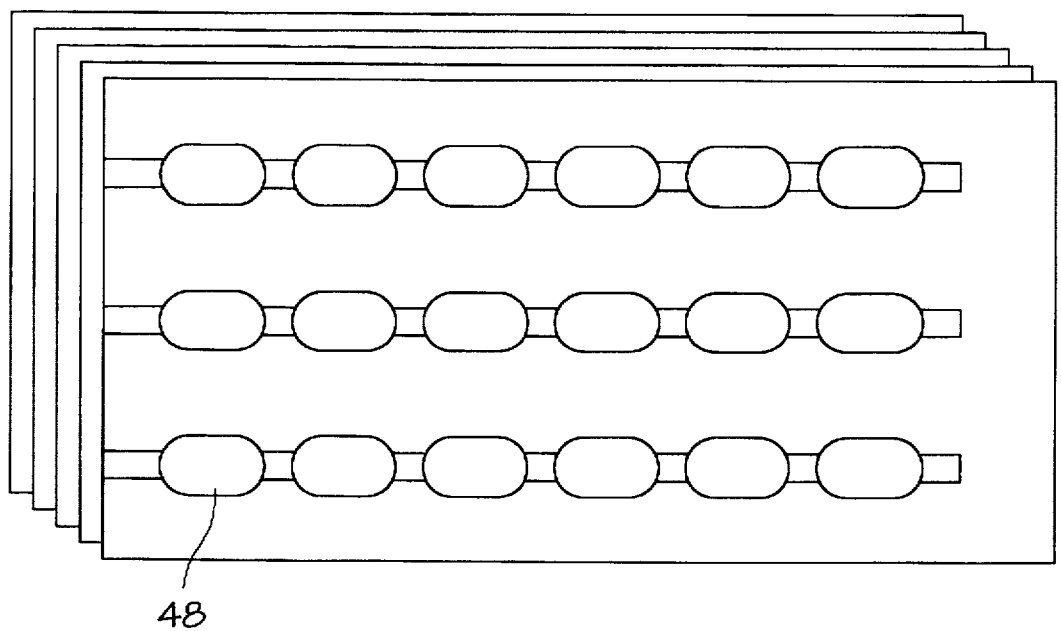
FIG. 13 is a template for the construction of a system configuration.

FIG. 13 illustrates a stack of installation templates for the embodiment according to FIG. 1. The templates are preferably in the form of sheets having openings (48) for accommodating the connecting device of the base plate. Each opening discloses the type of module to be connected-up. Connection of a sequence is effected simply by placing the template over the base plate and then connecting-up the modules. To assist people with defective vision, the openings may be provided with detectors which produce an alarm when the wrong module is placed in an opening. Alternatively, those openings which shall not be used may be closed with a padlock or some other type of barrier.

FIGS. 14–17 illustrate principles of further embodiments of the invention. Different functions of the modules shown are illustrated with the aid of centrally positioned rectangles, ovals, triangles, etc. The functions may be the same type of functions as those described above. Flow lines and flow channels have been shown in heavy (bold) lines. Solid black triangles represent valve functions that divide or join flows. As with the embodiments according to FIGS. 1 and 4, connecting means and end-connecting means shall match one another geometrically and functionally. The connecting devices and/or end-connecting means illustrated may also be provided with closure devices in analogy to the embodiment given in FIGS. 4a–c.

Figure 14:
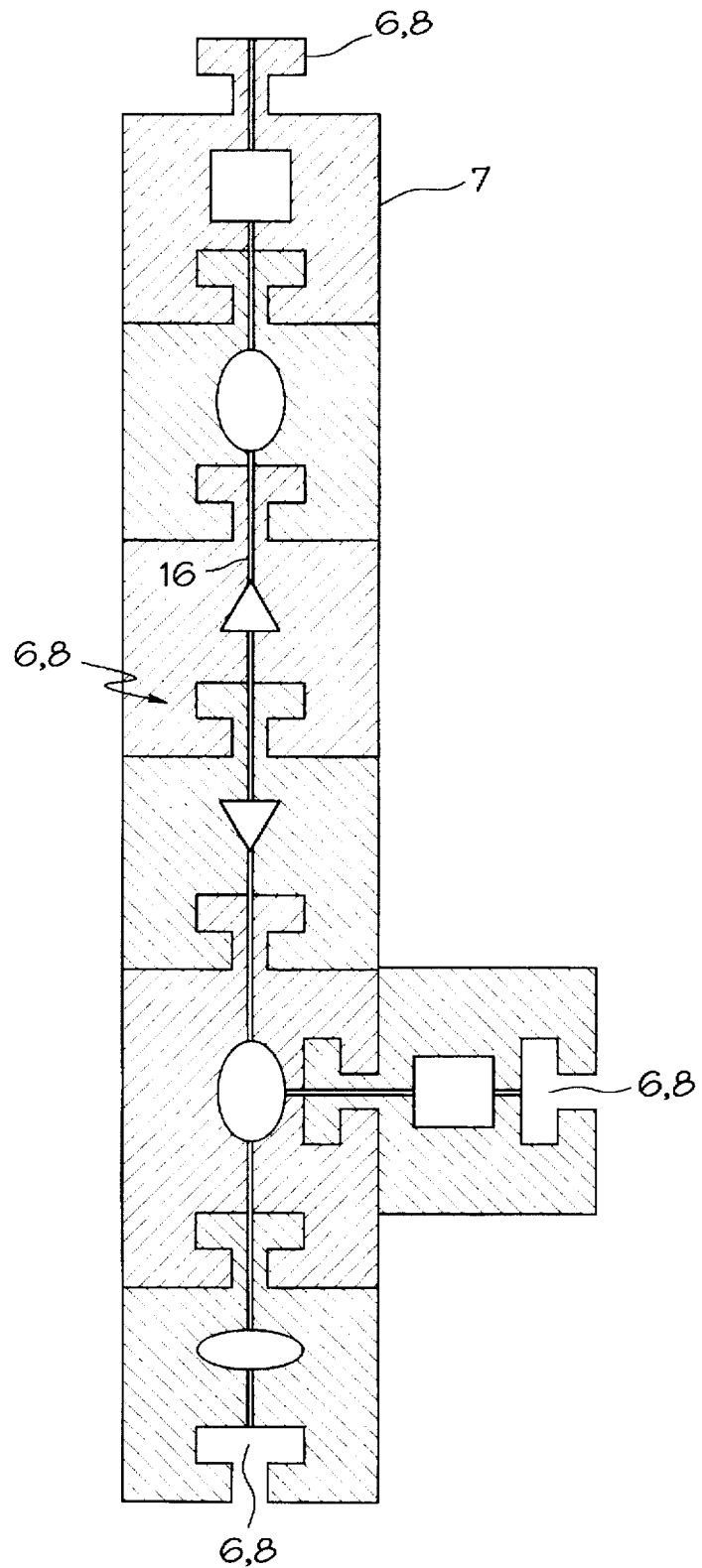
FIGS. 14–17 illustrate four alternative variants of the embodiments illustrated in FIGS. 1–12. The variants illustrated in FIGS. 14 and 17 have a flow line which is defined by the flow channels and functions of connected modules. The flow line illustrated in FIGS. 15 and 16 also includes intermediate segments which are attached to a stand or a base plate.

FIG. 14 illustrates an embodiment that lacks the base plate. The system formed by connected-up modules is self-supporting. End-connecting means (8) are coincident with connecting devices (6) or vice versa. The modules have flow channels (16). The flow line corresponding to the flow line (5) of FIGS. 1 and 4 is in this embodiment defined by the flow channels of co-linked modules. The end-connecting means of the modules may be shaped in the same manner as shown in FIGS. 4a–c (not shown in FIG. 14). The modules may be provided with a valve function, for instance in the same way as that described above with reference to FIGS. 4a–c.

Figure 15:
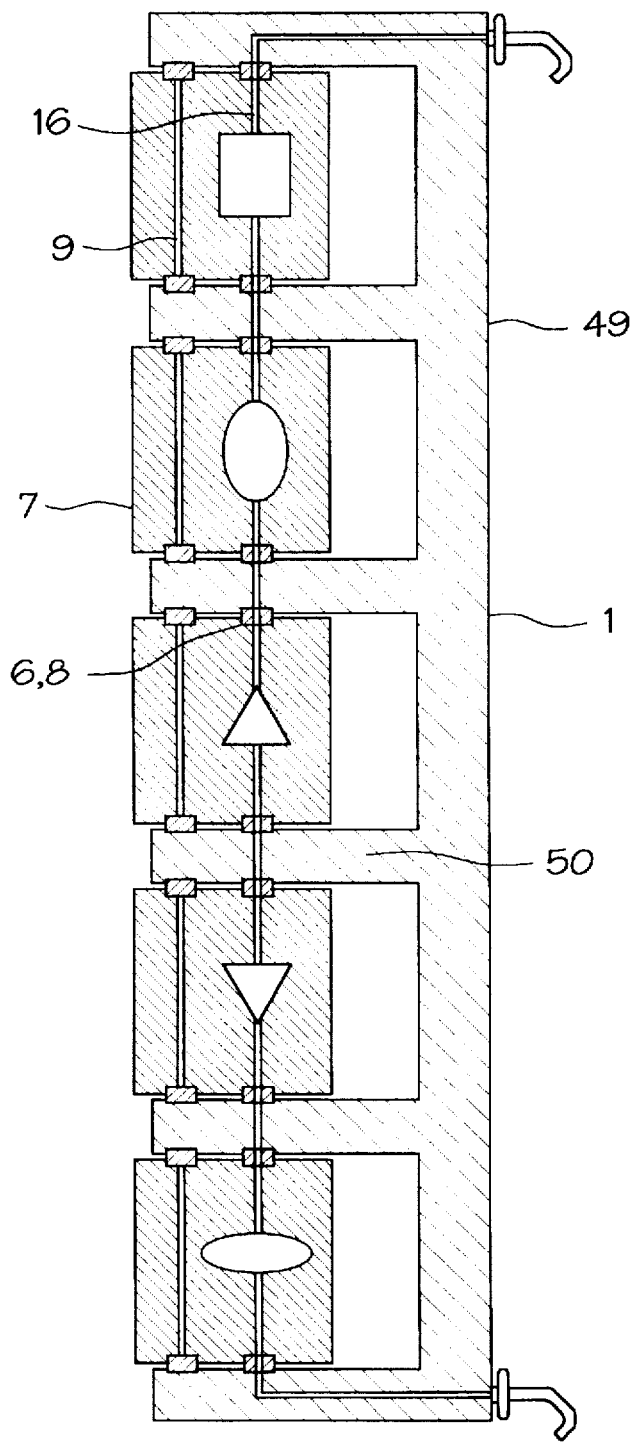

FIG. 15 illustrates a variant of the invention which includes a stand or a base plate (1) in which a flow line segment (49) is fixedly mounted. The modules (7) can be connected-up by moving the modules in the direction of the double-headed arrow. The modules have two flow channels (9 and 16). The channel (9) forms a flow bypass and the channel 16 connects the chromatography function of the module to the fixed segments (49). The flow-line segments (49) and the flow channels (9) correspond to the flow line (5) in FIGS. 1 and 4.

Connecting devices/end-connecting means, including sealing elements, are shown in FIG. 15 as solid rectangles (6 and 8). Movement of the modules in the aforedescribed manner results in a valve function. The outwardly projecting parts (50) may be detachable, so as to provide room for longer modules, for instance longer separation modules.

Figure 16:
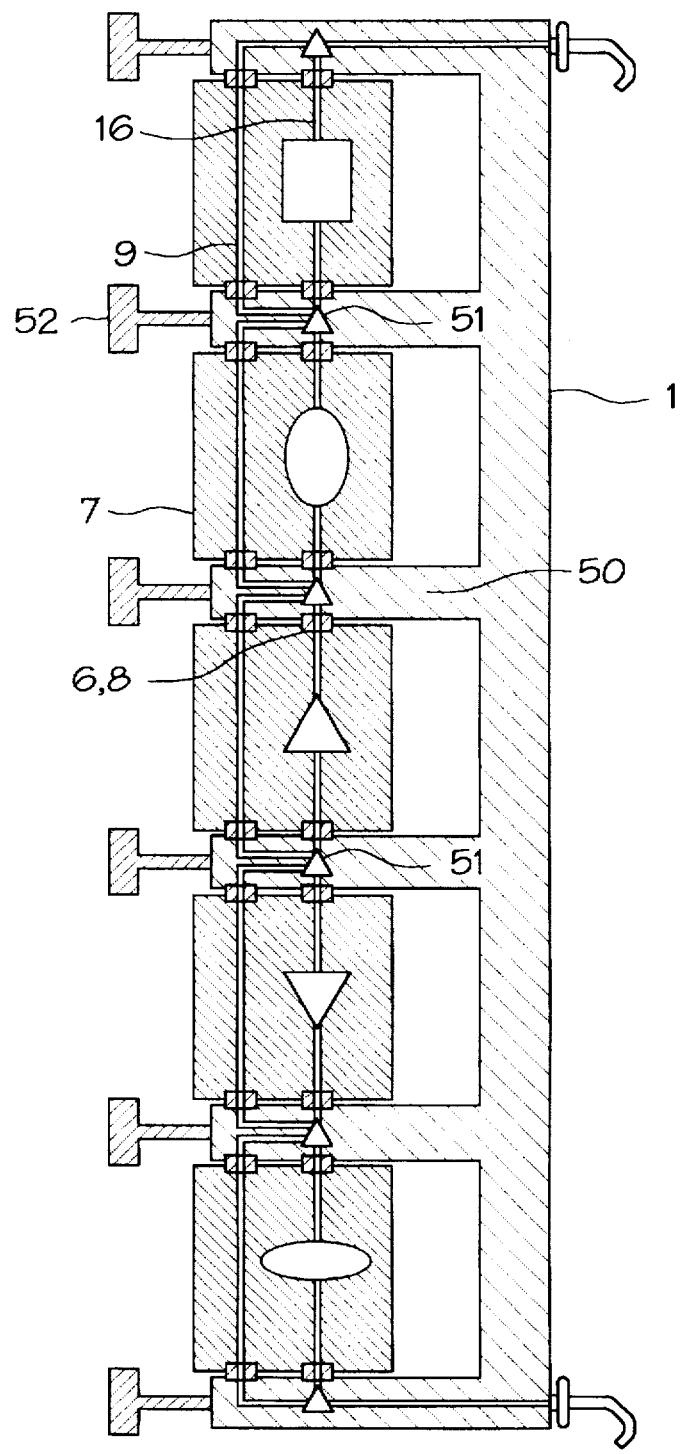

FIG. 16 is a variant of the invention which includes a stand or a base plate (1) in which there is mounted flow-line segments in outwardly projecting parts similar to FIG. 15 (49 and 50) having valve functions (51) which can be controlled manually by control means (52) or automatically with the aid of a computer (see the aforegoing with regard to FIGS. 1 and 4). The modules (7) can be connected-up, by moving the modules in the manner described with reference to FIG. 15. The modules have two flow channels (9 and 16). The channel (9) serves to bypass the flow while the channel 16 connects the chromatography function of the module to the flow line segment (49). Correspondence to the flow line (5) in FIGS. 1 and 4 is found in the flow-line segments (49) in the outwardly projecting parts (50) and the flow channels (9). Connecting means/end-connecting means, including any sealing elements, are illustrated in the Figure by solid rectangles (6 and 8). Similar to the FIG. 15 embodiment, the outwardly projecting parts (50) may be detachable.

Figure 17:
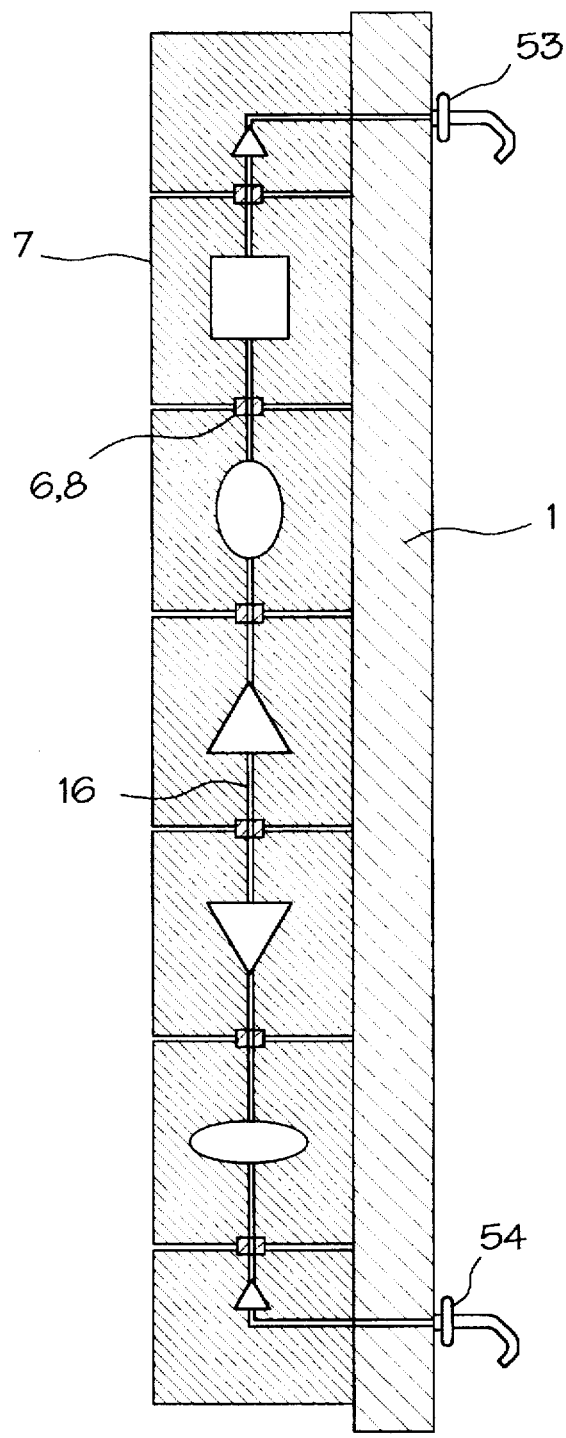

FIG. 17 illustrates a variant in which the modules (7) are detachably connected to a base plate which includes supply flow and exhaust flow (53 and 54 respectively). The flow line between the supply flow and exhaust flow is defined by the flow channels of the mutually connected modules. Compare the above concerning FIG. 14. Connecting devices/end-connecting means, including any sealing elements and possible valve functions, are illustrated in the Figure by solid rectangles (6 and 8).

We claim:

1. A liquid chromatographic system, comprising (a) at least two modules, one of the two modules comprising a separation module and the other of the two modules comprising an ancillary module having a non-separation function, (b) at least one fluid flow line, and (c) at least two connector devices provided along the flow line respectively connecting the modules to the flow line, wherein each of the modules includes at least one end connector fit into the respective connector device and each end connector is adapted to interchangeably fit into either connector device.

2. A liquid chromatographic system according to claim 1, wherein the module end connectors and the connector devices form quick coupling connections.

3. A liquid chromatographic system according to claim 1, wherein the ancillary module has at least one function selected from the group consisting of filtration, connection for an external unit, valve function, conductor for liquid flow between two connector or flow devices, injection port function, a sample loop function, detection and a stop function, optionally in combination with a chromatographic separation function.

4. A liquid chromatographic system according to claim 1, wherein the separation module includes one or two end connectors and the end connectors are provided with flow channels for conducting fluid flow to and from a separation medium arranged in the separation module.

5. A liquid chromatographic system according to claim 1, further comprising conductors for transmitting signals or power to the modules.

6. A liquid chromatographic system according to claim 5, further comprising at least one integrated signal processing unit.

7. A liquid chromatographic system according to claim 1, wherein each connector device includes a valve for connecting flow to the respective module associated with the end connecter which is fit in the connector device.

8. A liquid chromatographic system according to claim 1, wherein each connector device includes a flow bypass channel.

9. A liquid chromatographic system as defined by claim 1, wherein the system is free of tubing bundles.

10. A liquid chromatographic system as defined by claim 1, further comprising a template adapted to fit over a surface of the system and having openings for accommodating the connector devices.

11. A liquid chromatographic system as defined by claim 1, wherein the fluid flow line is contained in a base plate.

12. A liquid chromatographic system, as defined by claim 1, wherein each connector device includes a portion of the fluid flow line and adjacent connector devices are connected with one another to form the respective portions of the fluid flow line.

13. A liquid chromatographic system, comprising (a) at least two modules, one of the two modules comprising a separation module and the other of the two modules comprising an ancillary module, (b) at least one fluid flow line, and (c) at least two connector devices provided along the flow line respectively connecting the modules to the flow line, wherein each of the modules includes at least one end connector fit into the respective connector device and each end connector is adapted to interchangeably fit into either connector device, and further wherein the ancillary module includes at least one function selected from the group consisting of filtration, connection for an external unit, valve function, conductor for liquid flow between two connector or flow devices, injection port function, sample loop function, detection and a stop function.

14. A liquid chromatographic system according to claim 13, wherein the module end connectors and the connector devices form quick coupling connections.

15. A liquid chromatographic system according to claim 13, wherein the ancillary module further includes a chromatographic separation function.

16. A liquid chromatographic system according to claim 13, wherein the separation module includes one or two end connectors and the end connectors are provided with flow channels for conducting fluid flow to and from a separation medium arranged in the separation module.

17. A liquid chromatographic system according to claim 13, further comprising conductors for transmitting signals or power to the modules.

18. A liquid chromatographic system according to claim 17, further comprising at least one integrated signal processing unit.

19. A liquid chromatographic system according to claim 13, wherein each connector device includes a valve for connecting flow to the respective module associated with the end connecter which is fit in the connector device.

20. A liquid chromatographic system according to claim 13, wherein each connector device includes a flow bypass channel.

* * * * *